(12) United States Patent
Radzinsky

(10) Patent No.: US 7,722,679 B2
(45) Date of Patent: May 25, 2010

(54) FLEXIBLE PRONG LAMINATING ADAPTOR FOR USE IN CREATING A LAMINATED STUMP SOCKET FOR ATTACHING A PROSTHETIC LIMB

(76) Inventor: Vladimir Radzinsky, 248 So. Doheny Dr., Apt. 5, Beverly Hills, CA (US) 90211

( * ) Notice: Subject to any disclaimer, the term of this patent is extended or adjusted under 35 U.S.C. 154(b) by 327 days.

(21) Appl. No.: 11/517,091

(22) Filed: Sep. 7, 2006

(65) Prior Publication Data

US 2008/0275570 A1    Nov. 6, 2008

(51) Int. Cl.
*A61F 2/60* (2006.01)
(52) U.S. Cl. ........................................ 623/33
(58) Field of Classification Search ............ 623/22.21, 623/32, 33; 403/7
See application file for complete search history.

(56) References Cited

U.S. PATENT DOCUMENTS

| | | | |
|---|---|---|---|
| 5,201,773 A | 4/1993 | Carideo, Jr. | |
| 5,545,232 A | 8/1996 | Van de Veen | |
| 5,593,456 A | 1/1997 | Merlette | |
| 6,340,370 B1 * | 1/2002 | Willert et al. | 623/22.38 |
| 2003/0171818 A1 * | 9/2003 | Lewallen | 623/22.22 |
| 2004/0102856 A1 * | 5/2004 | Hellberg | 623/33 |
| 2004/0204770 A1 * | 10/2004 | Curtis | 623/33 |

* cited by examiner

*Primary Examiner*—Bruce E Snow
*Assistant Examiner*—Melissa Montano
(74) *Attorney, Agent, or Firm*—Christie, Parker & Hale, LLP

(57) ABSTRACT

A socket adaptor, for use in creating a laminated stump socket for use with a patient having a stump, in attaching a prosthetic limb to the patient. The socket adaptor has a main body and a plurality of prongs. The prongs are made of sheet titanium so that they are flexible and bendable to closely accommodate the stump. The socket adaptor is subsequently encapsulated with the laminated stump socket. The main body allows a prosthetic connector to be attached thereto to allow the laminated stump socket to secure directly to the prosthetic limb.

12 Claims, 6 Drawing Sheets

FLEXIBLE PRONG LAMINATING ADAPTOR FOR USE IN CREATING A LAMINATED STUMP SOCKET FOR ATTACHING A PROSTHETIC LIMB

BACKGROUND OF THE INVENTION

The invention relates to a socket adaptor for attaching a prosthetic limb. More particularly, the invention relates to a socket adaptor that has flexible prongs that allow the socket adaptor to be readily conformed to a stump casting to a stump and allow subsequent attachment of a prosthetic limb.

Three prong laminating adaptors are often used in the prosthetic industry in the creation of laminated stump sockets. The laminated stump socket is fit over the stump of the patient, and is configured to allow the prosthetic device to be attached thereto. Accordingly the laminated stump socket must both fit comfortably on the stump, and have sufficient structural integrity to create a reliable connection to the prosthetic device. And of course, compatible hardware must be present to create the requisite connection to the prosthetic device.

To provide for these dual goals, the standard three prong adaptor has a threaded opening that allows a "pyramid" to be threaded thereinto; and has prongs that are pre-formed into a downward arc to approximately conform to the distal end of the stump. These three prong adaptors are made of cast heat-treated stainless steel, and thus are rigid and brittle. Prosthetists, in attempt to make the patient more comfortable by making the socket fit better, will try to bend the prongs to make them better conform to the stump. Attempts to bend the prongs, however, either result in an immediate fracture, or create cracks that weaken the integrity of the adaptor and result in later breakage and shearing with continued usage.

U.S. Pat. No. 5,201,773 to Carideo, Jr.; U.S. Pat. No. 5,545,232 to Van de Veen; and U.S. Pat. No. 5,593,456 to Merlette disclose prosthetic limbs and devices that have an integral socket for the stump. Such devices do not allow variation of the prosthetic device and have a very limited ability to adapt to the stump of the patient.

While these units may be suitable for the particular purpose employed, or for general use, they would not be as suitable for the purposes of the present invention as disclosed hereafter.

SUMMARY OF THE INVENTION

It is an object of the invention to produce a socket adaptor that facilitates secure attachment of a prosthetic limb or device. Accordingly the socket adaptor has three flexible prongs that are initially co-planar, and can be bent to conform to the contours of the stump.

It is another object of the invention to provide a socket adaptor in which the flexible prongs can be bent and manipulated into any desired position—numerous times—without breaking. Accordingly, the flexible prongs are made of sheet titanium, which possesses sufficient strength and flexibility to fulfill its intended function.

It is yet a further object of the invention to provide a socket adaptor that is manufactured for a long useful life with superior structural integrity. Accordingly, the main body of the socket adaptor is made of solid titanium.

The invention is a socket adaptor, for use in creating a laminated stump socket for use with a patient having a stump, in attaching a prosthetic limb to the patient. The socket adaptor has a main body and a plurality of prongs. The prongs are made of sheet titanium so that they are flexible and bendable to closely accommodate the stump. The socket adaptor is subsequently encapsulated with the laminated stump socket. The main body allows a prosthetic connector to be attached thereto to allow the laminated stump socket to secure directly to the prosthetic limb.

To the accomplishment of the above and related objects the invention may be embodied in the form illustrated in the accompanying drawings. Attention is called to the fact, however, that the drawings are illustrative only. Variations are contemplated as being part of the invention, limited only by the scope of the claims.

BRIEF DESCRIPTION OF THE DRAWINGS

In the drawings, like elements are depicted by like reference numerals. The drawings are briefly described as follows.

DETAILED DESCRIPTION OF THE PREFERRED EMBODIMENTS

Figure 1:
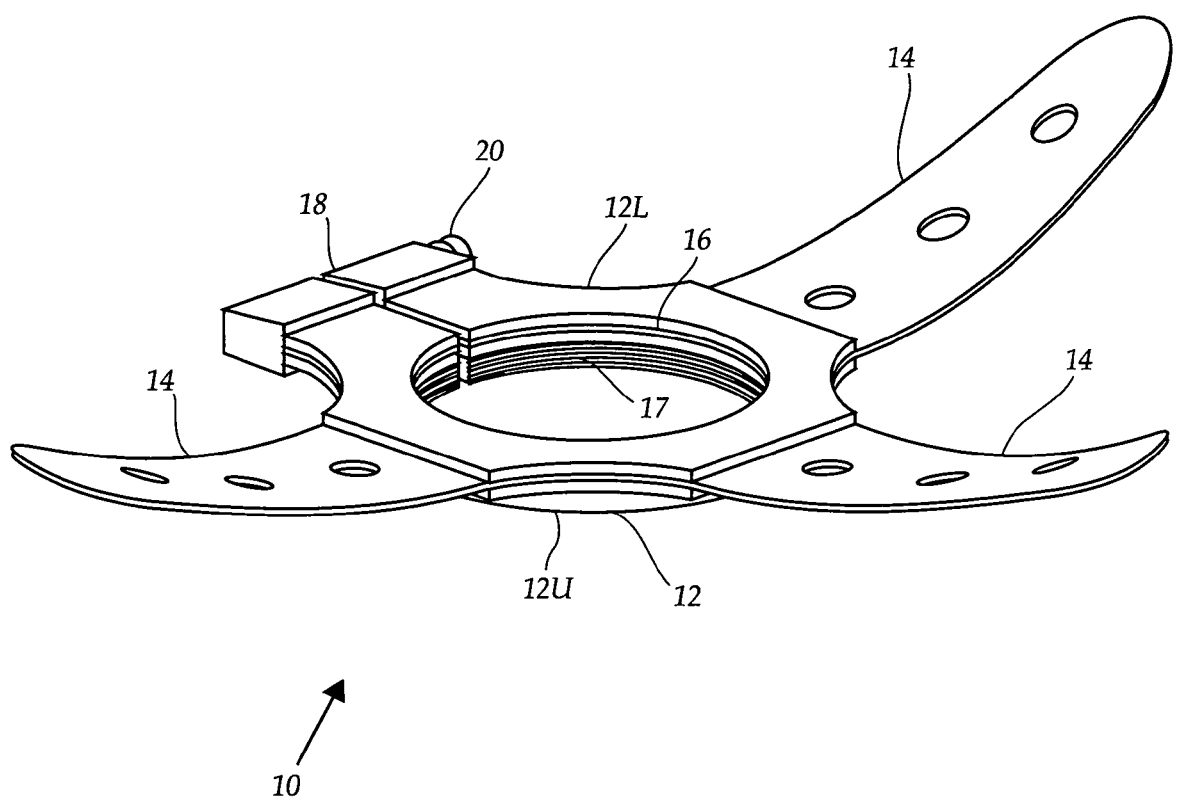
FIG. 1 is a diagrammatic perspective view, illustrating a lower surface of a socket adaptor.
Figure 2:
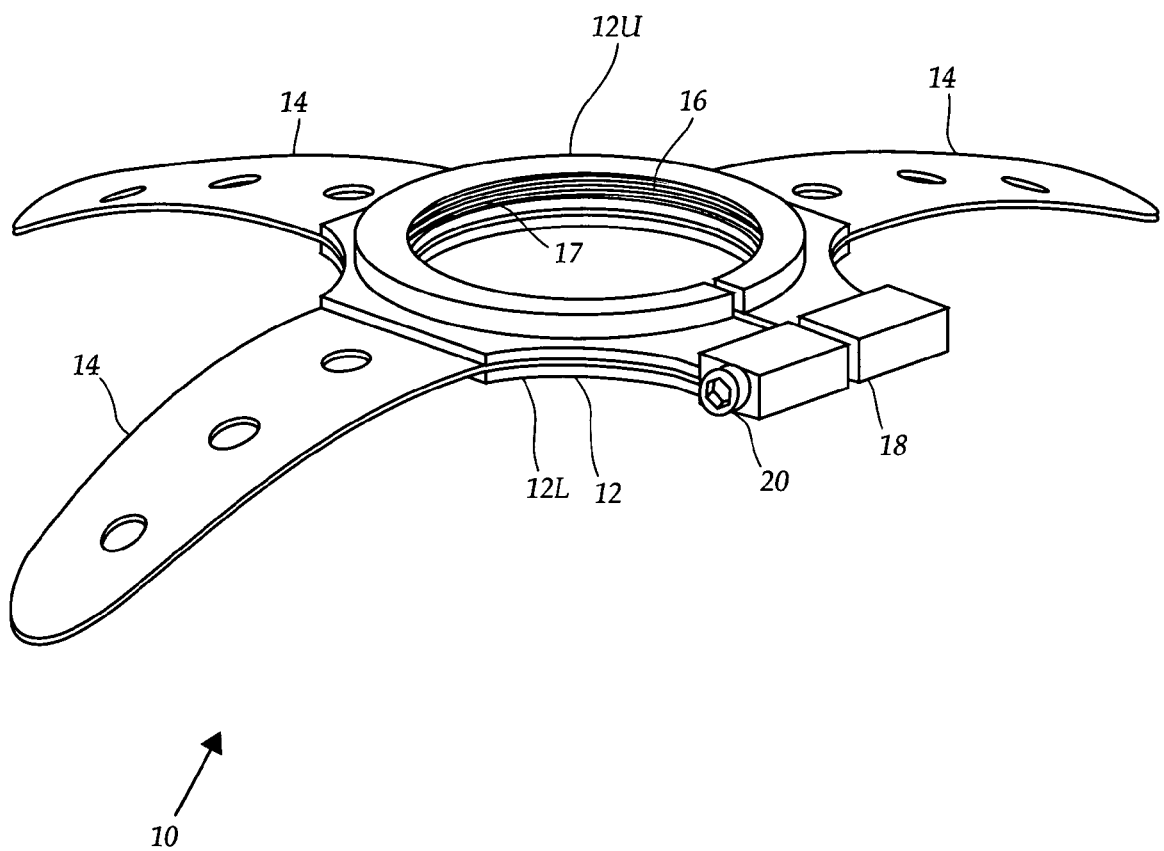
FIG. 2 is a diagrammatic perspective view, illustrating an upper surface of the socket adaptor of FIG. 1.

FIG. 1 and FIG. 2 illustrate a socket adaptor 10 for use in the creation of a laminated stump socket, for attaching a prosthetic limb or device to a patient. The socket adaptor 10 includes a main body 12, and three prongs 14 extending outwardly from the main body 12.

The main body 12 has a lower surface 12L, and an upper surface 12U. A main bore 16 extends fully between the upper surface 12U and lower surface 12L. The main bore 16 is internally threaded 17, and may be selectively adjusted with an adjustment opening 18 that allows the main bore 16 to be slightly spread and narrowed and an adjustment screw 20 that regulates the magnitude of the adjustment opening 18. In particular, the adjustment screw 20 allows a device to be threaded into the main bore 16 and then prevented from unthreading by tightening the adjustment screw 20 to narrow the adjustment opening 18 and thus cause the main bore 16 to clamp upon the item.

Figure 3:
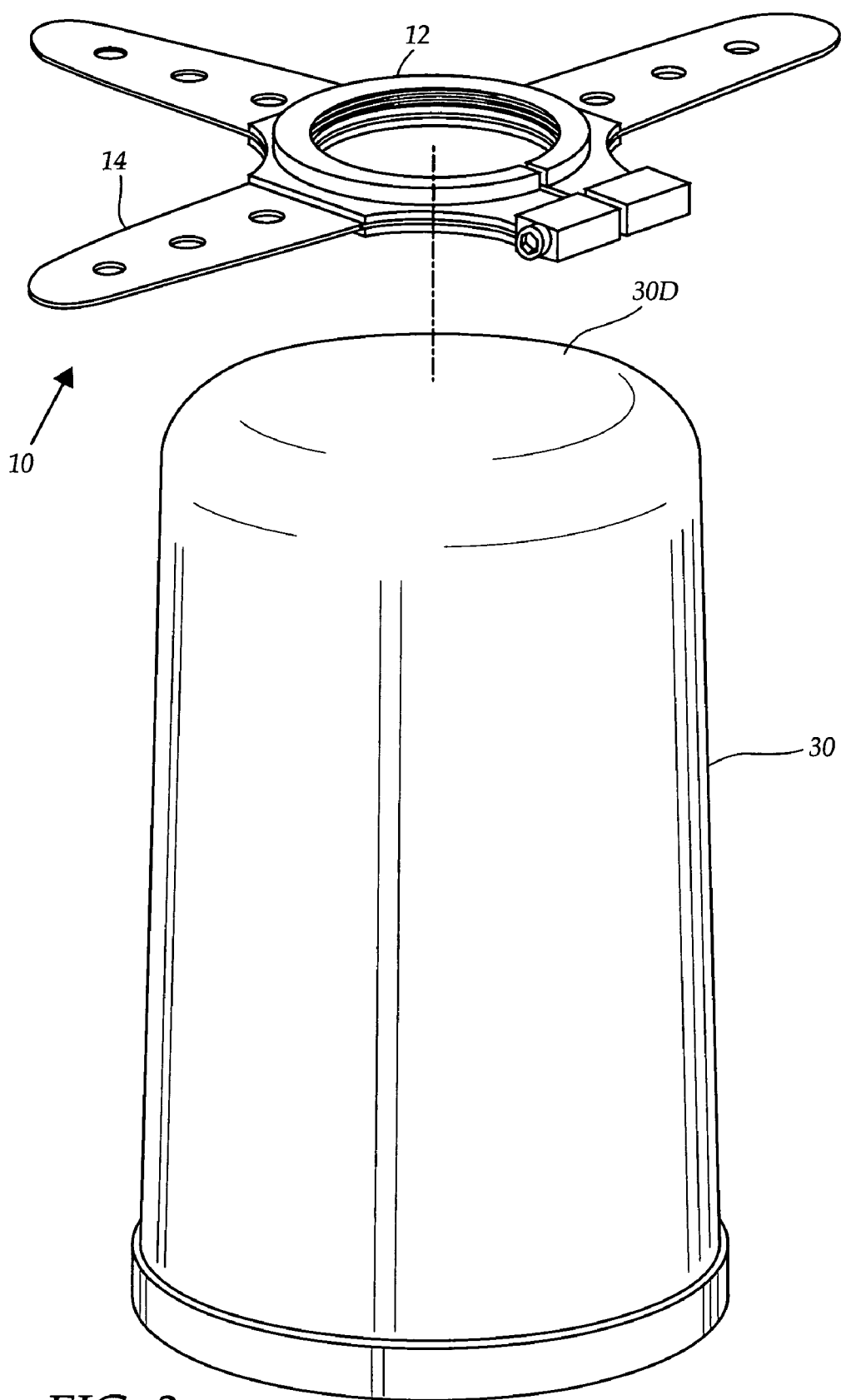
FIG. 3 is a diagrammatic perspective view, illustrating the adaptor according to the present invention in an original, unbent state, being fitted unto a stump casting.

FIG. 3 illustrates the socket adaptor 10 according to the present invention, wherein the prongs 14 initially extend radially outwardly from the main body 12 in a common plane. The prongs 14 are each broad and flat, and substantially parabolic in shape, having a curved extremity. The socket adaptor 10 may be manufactured such that the prongs 14 initially extend in a co-planar configuration because the prongs 14 are flexible and thus bendable-allowing them to be set as desired by the prosthetist in fitting the patient. To facilitate such bendability, the prongs are made of sheet titanium. The use of sheet titanium material has the unexpected result of making the prongs extremely strong, yet able to bend into the desired configuration. A suitable thickness for the sheet titanium has been discovered to be approximately 0.5 mm, although other thicknesses are also suitable and thus may also be used.

In FIG. 3, the socket adaptor 10 is shown positioned immediately above a stump casting 30, having a distal end 30D. The stump casting 30 is created from a stump belonging to the patient for which the laminated stump socket is intended. The creation of the stump casting 30 allows the prosthetist to work without requiring the patient to be present and thereby facilitates making a laminated stump socket that precisely fits the stump of the patient.

Figure 4:
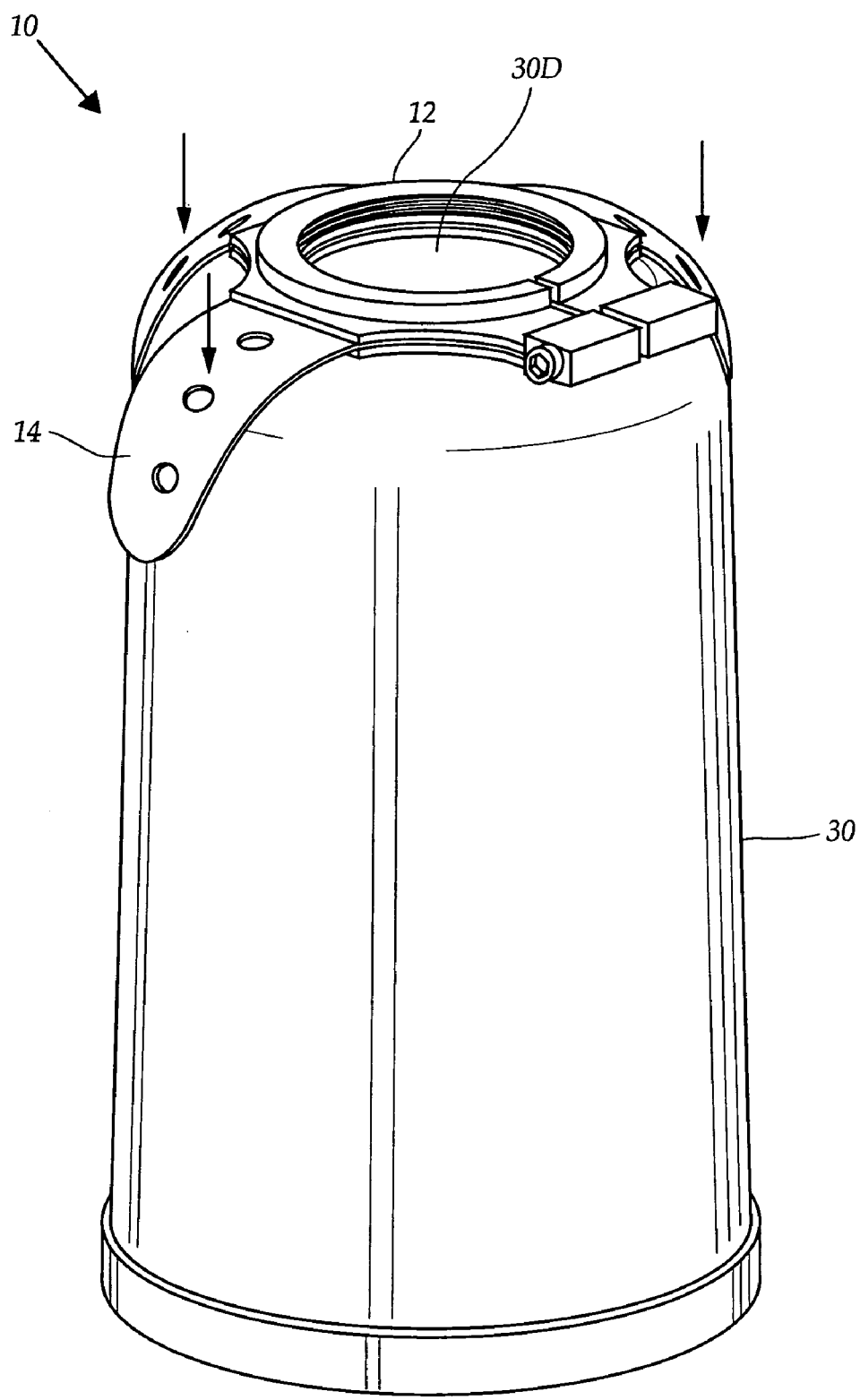
FIG. 4 is a diagrammatic perspective view, similar to FIG. 3, except wherein the adaptor prongs are being bent to conform with the stump casting.

FIG. 4 illustrates the socket adaptor 10 being customized for the patient. In particular, the main body 12 is positioned against the distal end 30D of the stump casting 30, and the prongs 14 of the socket adaptor 10 previously illustrated in FIG. 3 are being bent downwardly to conform to the distal end 30D of the stump casting 30. Since the prongs 14 of the present invention are made of sheet titanium, the bending can be repeated until a precise fit is obtained.

Figure 5:
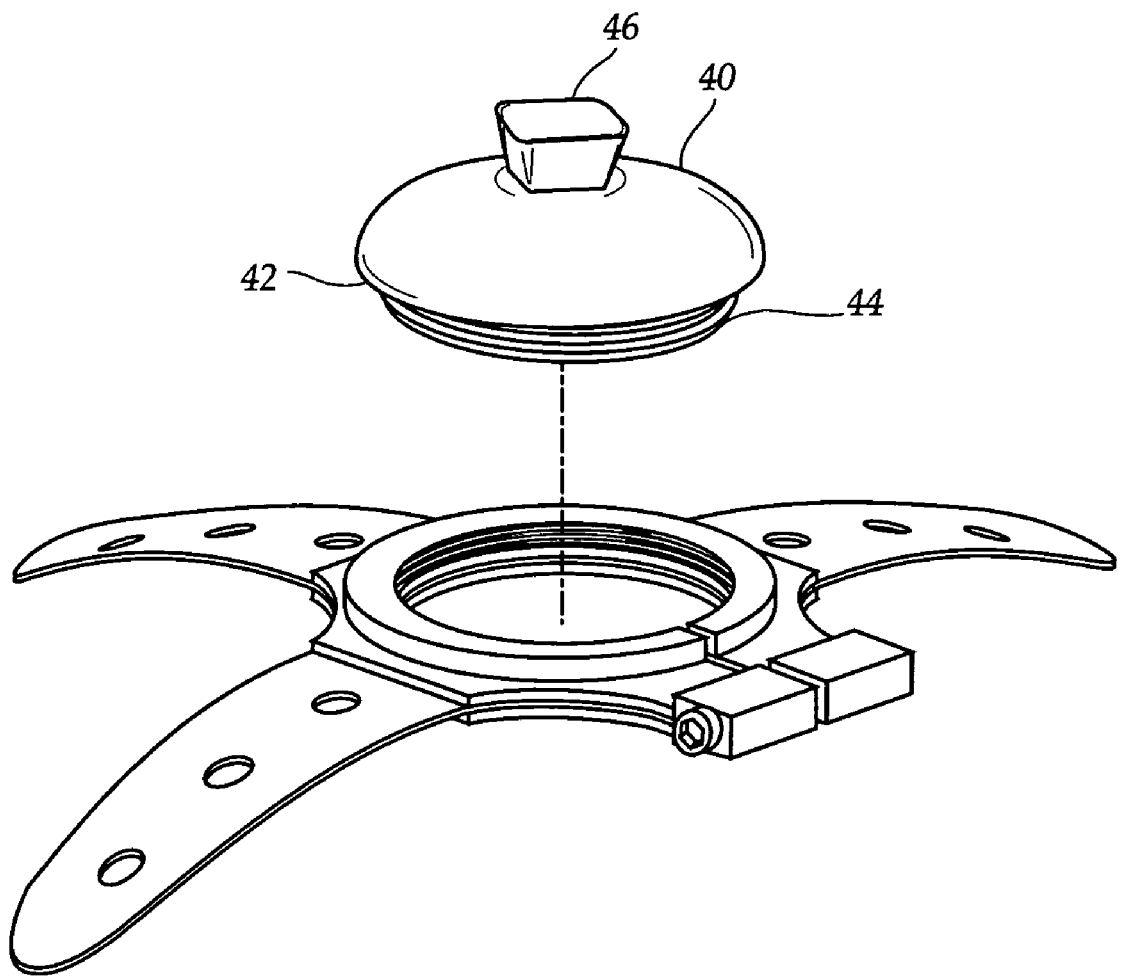
FIG. 5 is a diagrammatic perspective view, illustrating a prosthetic connector being threaded into the adaptor.

FIG. 5 illustrates a prosthetic connector 40 having a round base 42 with a threaded portion 44 and a pyramid plug 46. The pyramid plug 46 allows connection of various prosthetic devices having hardware that is configured to attach thereto. The pyramid plug 46 may be substituted with other configurations that are adapted to connect to prosthetic devices having different connection hardware. It should be noted that according to a preferred embodiment, the main body 12 is made of solid titanium, as is the prosthetic connector 40.

Figure 6:
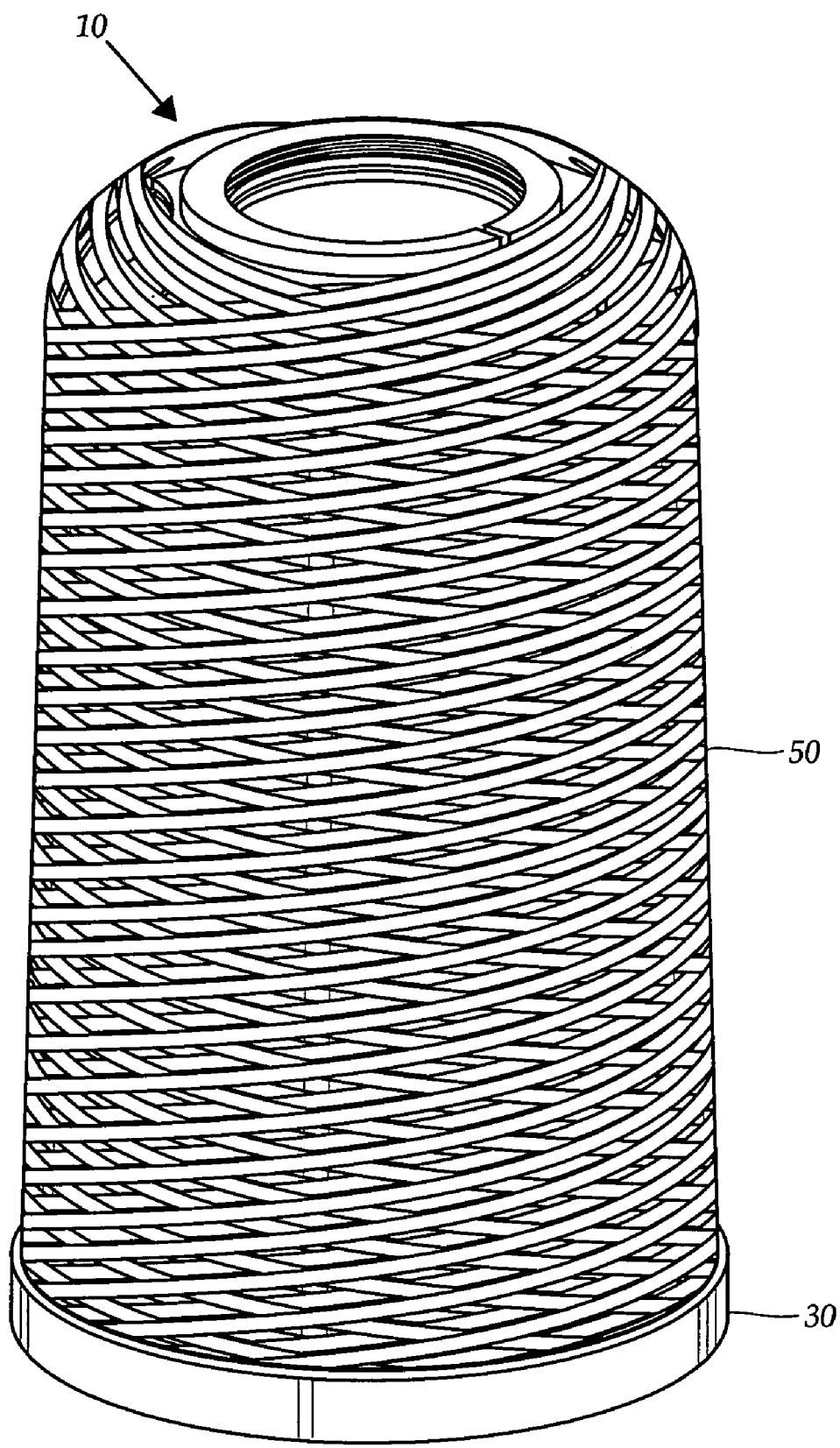
FIG. 6 is a diagrammatic perspective view, illustrating the stump casting and adaptor prongs being covered with a graphite weave, prior to being coated with resin.

FIG. 6 illustrates the socket adaptor 10, fitted onto the stump casting 30, and covered with graphite mesh 50. The graphite mesh 50 is subsequently coated with resin to encapsulate the socket adaptor 10 and create a hardened, shell-like surface which is then removed from the stump casting 30 and is permanently formed to fit the stump of the patient. Most importantly, by using the socket adaptor 10 of the present invention, the laminated stump socket thus created closely adapts to the stump of the patient, for a comfortable fit, without sacrificing the structural integrity of the socket adaptor 10 encapsulated therein.

In conclusion, herein is presented a socket adaptor that contains flexible prongs that allow a superior laminated stump socket to be created. The invention is illustrated by example in the drawing figures, and throughout the written description. It should be understood that numerous variations are possible, while adhering to the inventive concept. Such variations are contemplated as being a part of the present invention.

What is claimed is:

1. A socket adaptor for use in creating a laminated stump socket, comprising:
a separate main body comprising a first section and a second section being spaced apart to define a gap and a separate plurality of flexible prongs that are partly located inside the gap and permanently affixed to the main body, the main body having a prosthetic connector for securing to a prosthetic limb, the prongs being made of flexible sheet titanium so that they are substantially flat, flexible, and bendable and being adapted to be flexed and bent repeatedly to conform to be fitted to a stump socket without weakening the prongs.

2. The socket adaptor as recited in claim 1, wherein the prosthetic connector has a threaded base, and wherein the main body has a main bore for accepting the prosthetic connector.

3. The socket adaptor as recited in claim 2, wherein the main body is made of titanium having different material property than the sheet titanium of the flexible prongs.

4. The socket adaptor as recited in claim 2, wherein the main body has an adjustment opening that allows the main bore to be slightly spread and narrowed, and an adjustment screw for selectively narrowing the main bore to clamp onto the threaded base of the prosthetic connector when threaded in the main bore.

5. The socket adaptor as recited in claim 1, wherein the prosthetic connector has a pyramid plug for securing to the prosthetic limb.

6. The socket adaptor as recited in claim 1, wherein the main body is made of solid titanium.

7. The socket adaptor as recited in claim 1, wherein the flexible prongs made of flexible sheet titanium are affixed to the main body made of solid titanium, and wherein bending, flexing and manipulation of the prongs repeatedly does not fracture, crack or weaken the prongs.

8. The socket adaptor as recited in claim 1, wherein the prongs have a thickness of about 0.5 mm.

9. A socket adaptor, for use in creating a laminated stump socket for attaching a prosthetic limb to a patient having a stump using a prosthetic connector having a plug, the socket adaptor comprising:
a separate main body and a plurality of flexible prongs that are permanently affixed to the main body, the main body being adapted for accepting a prosthetic connector for securing to the prosthetic limb, the prongs being made of flexible sheet titanium and being substantially flat, wherein the flexible sheet titanium has a different material property than a material property of the main body such that the flexible sheet titanium is more flexible and bendable than the main body, and wherein the prongs extend radially outwardly from the main body in substantially a same plane as the main body and are adapted to be flexed to conform to be fitted to a stump socket; and
wherein the main body comprises a first section and a second section being spaced apart to define a gap, and wherein the plurality of flexible prongs are at least partly located inside the gap.

10. The socket adaptor as recited in claim 9, wherein the prongs have a thickness of about 0.5 mm.

11. A socket adaptor for use in creating a laminated stump socket for attaching a prosthetic limb to a patient having a stump using a prosthetic connector having a plug, the socket adaptor comprising:
a separate main body and a plurality of flexible prongs that are permanently affixed to the main body, the main body being adapted for accepting a prosthetic connector for securing to the prosthetic limb, the prongs being made of flexible sheet titanium and being substantially flat, flexible and bendable;
wherein each prong is bendable from a first position wherein the prong is substantially flat and extends radially outward from the main body in a plane defining the main body to a second position wherein a substantial portion of the prong is oriented transverse to the plane defining the main body;
wherein each prong is bendable by hand from the first position to the second position without using a tool; and
wherein the main body comprises a first section and a second section being spaced apart to define a gap, and wherein the plurality of flexible prongs are at least partly located inside the gap.

12. The socket adaptor as recited in claim 11, wherein the prongs have a thickness of about 0.5 mm.

* * * * *